United States Patent
Schmidt et al.

(10) Patent No.: US 10,624,540 B2
(45) Date of Patent: Apr. 21, 2020

(54) METHOD AND INSTRUMENT FOR SURGICAL NAVIGATION

(71) Applicant: MOELLER-WEDEL GMBH, Wedel (DE)

(72) Inventors: Martin Schmidt, Bad Schwartau (DE); Jochen Koetke, Hamburg (DE); Peter Schalt, Moorrege (DE); Stefan Oelkers, Berlin (DE); Rolf-Rainer Grigat, Halstenbek (DE); Thomas Hoell, Buehl (DE)

(73) Assignee: Moeller-Wedel GmbH, Wedel (DE)

( * ) Notice: Subject to any disclaimer, the term of this patent is extended or adjusted under 35 U.S.C. 154(b) by 516 days.

(21) Appl. No.: 14/635,974

(22) Filed: Mar. 2, 2015

(65) Prior Publication Data

US 2015/0164329 A1   Jun. 18, 2015

Related U.S. Application Data

(60) Division of application No. 12/831,849, filed on Jul. 7, 2010, now abandoned, which is a
(Continued)

(30) Foreign Application Priority Data

Jun. 13, 2002   (DE) .................................. 102 26 361
Oct. 21, 2002   (DE) .................................. 102 49 025

(51) Int. Cl.
| | | |
|---|---|---|
| *A61B 5/00* | (2006.01) | |
| *A61B 34/20* | (2016.01) | |
| *A61B 90/20* | (2016.01) | |
| *A61B 90/00* | (2016.01) | |
| *A61B 34/10* | (2016.01) | |
| *A61B 5/107* | (2006.01) | |

(52) U.S. Cl.
CPC .......... *A61B 5/0042* (2013.01); *A61B 5/0077* (2013.01); *A61B 5/1079* (2013.01);
(Continued)

(58) Field of Classification Search
None
See application file for complete search history.

(56) References Cited

U.S. PATENT DOCUMENTS

| | | |
|---|---|---|
| 5,305,091 A | 4/1994 | Gelbert et al. |
| 5,352,233 A | 10/1994 | Anis |

(Continued)

FOREIGN PATENT DOCUMENTS

WO   01/43654   6/2001

*Primary Examiner* — Peter Luong
(74) *Attorney, Agent, or Firm* — Alix, Yale & Ristas, LLP

(57) ABSTRACT

An operating microscope including an optical unit for forming an image of an object plane in oculars of the microscope, an optoelectronic image receiver coupled to the microscope and optics to form images, of objects placed in a region between a front objective of the microscope and an object plane of the microscope, on the optoelectronic image receiver. The microscope has a magnification factor of the optics to form images, and a system to detect optical markings forming a markings pattern placed on a surgical instrument or an object placed in the region between the front objective of the microscope and the object plane of the microscope. The system calculates a geometrical position and orientation of the markings pattern in relation to the optoelectronic image receiver, relative to the microscope.

19 Claims, 5 Drawing Sheets

Related U.S. Application Data continuation-in-part of application No. 10/516,297, filed as application No. PCT/EP03/06130 on Jun. 11, 2003, now Pat. No. 7,912,532.

(52) U.S. Cl.
CPC .............. *A61B 34/10* (2016.02); *A61B 34/20* (2016.02); *A61B 90/20* (2016.02); *A61B 90/39* (2016.02); *A61B 2034/107* (2016.02); *A61B 2034/2051* (2016.02); *A61B 2034/2055* (2016.02); *A61B 2034/2057* (2016.02); *A61B 2034/2065* (2016.02); *A61B 2034/2068* (2016.02); *A61B 2090/363* (2016.02); *A61B 2090/364* (2016.02); *A61B 2090/371* (2016.02); *A61B 2090/3937* (2016.02); *A61B 2090/3983* (2016.02); *A61B 2576/026* (2013.01)

(56) References Cited

U.S. PATENT DOCUMENTS

| | | |
|---|---|---|
| 5,545,160 A | 8/1996 | O'Rourke |
| 5,630,431 A | 5/1997 | Taylor |
| 5,712,732 A | 1/1998 | Street |
| 5,790,307 A | 8/1998 | Mick et al. |
| 5,792,147 A | 8/1998 | Evans et al. |
| 5,795,294 A | 8/1998 | Luber et al. |
| 5,795,295 A | 8/1998 | Hellmuth et al. |
| 5,807,387 A | 9/1998 | Druais |
| 5,971,997 A | 10/1999 | Guthrie et al. |
| 6,006,126 A * | 12/1999 | Cosman ................ A61B 34/20 600/414 |
| 6,036,637 A | 3/2000 | Kudo |
| 6,661,571 B1 | 12/2003 | Shioda et al. |
| 6,825,455 B1 * | 11/2004 | Schwarte ................ G01J 9/00 250/214.1 |
| 2001/0055062 A1 | 12/2001 | Shioda et al. |
| 2002/0002330 A1 | 1/2002 | Vilsmeier |
| 2002/0151784 A1 * | 10/2002 | Mizoguchi ......... G02B 21/0012 600/407 |
| 2003/0011677 A1 * | 1/2003 | Spink ..................... G01B 11/02 348/136 |
| 2004/0243147 A1 | 12/2004 | Lipow |
| 2004/0254454 A1 | 12/2004 | Kockro |
| 2006/0122516 A1 * | 6/2006 | Schmidt ................ A61B 90/36 600/476 |

* cited by examiner

METHOD AND INSTRUMENT FOR SURGICAL NAVIGATION

CROSS-REFERENCE TO RELATED APPLICATIONS

This application is a divisional application of U.S. Ser. No. 12/831,849, filed Jul. 7, 2010 which is a continuation-in-part application of U.S. Ser. No. 10/516,297, filed Dec. 19, 2005, now U.S. Pat. No. 7,912,532 issued Mar. 22, 2011. U.S. Ser. No. 10/516,297 is a national stage application of PCT/EP03/06130, filed Jun. 11, 2003, and claims priority to DE 102 49 025.2, filed Oct. 21, 2002, and DE 102 26 361.2, filed Jun. 13, 2002. The entire content of each is incorporated herein by reference.

BACKGROUND

Field of Invention

This disclosure relates to optimizing identification of a current position in surgical navigation, especially neuronavigation, in surgery with an operating microscope and at least one optoelectronic image receiver, which may also be integral or connectable to the microscope and a computer system.

Discussion of the Related Art

Neuronavigation deals with the planning, but also with the performance of trajectories for surgical intervention at the human brain, the spine and the like. To this end, tomographies of the patient are made preoperatively, with markings provided on the patient's body which will likewise be detected by the tomography. Directly before the operation the three-dimensional location of said markers in space is determined by navigation, and a reference between the anatomy of the patient and the preoperatively recorded data records is thus produced. A corresponding process is called registration. Basically, a difference between optical navigation methods and magnetically working methods can be made. Both methods serve to determine the three-dimensional location and orientation of a special navigational pointer instrument in space, which serves to tap on relevant points. The location of the pointer tip in known optically working systems is not detected directly, but is determined with the aid of markers which, in most cases, are attached to the pointer in the form of balls. In the known systems reflectors for infrared light generated by special infrared light radiation sources are used as markers or marker substances. Two cameras located on a tie-bar then record the images and determine the location of the pointer in space.

According to methods based on magnetic fields, the pointers comprise sensors which serve to detect the spatial location either from a generated magnetic alternating field or from a pulsed magnetic continuous field.

Optical systems have the disadvantage that there is the danger of the camera being covered by the operating staff. Magnetic systems fail to operate once objects made of soft iron are in the proximity thereof, which upset or distort the magnetic fields.

The basic object of the navigational systems available on the market resides in that—as was briefly outlined above—the position or the tip of an instrument, with which a detail in the field of operation is pointed to during the operation, is correlated with data from preoperative diagnostic methods, such as computerized tomography or magnetic resonance tomography. After such a correlation has taken place, for example, the position of a point in situs, to which the surgeon points with the aforementioned instrument during the operation, may be indicated to him in the images of the preoperative photographs in real-time. In this manner the surgeon obtains information with respect to the current position relative to a position of a structure recognizable in the CT- or MR-image, e.g. a tumor.

One possibility to represent this information to an operating surgeon is to register the position of the instrument tip in a previously selected CT- or MR-image as a point. For allowing the navigational system to fulfill this task, both the location and the orientation of the patient as well as those of the aforementioned surgical instrument must be known. As was explained, this information is, in current systems, detected for example by means of a pair of stereo cameras, which is located in the proximity of the operating table and detects the operating instrument.

Other known navigation systems moreover offer the possibility of overlapping images from preoperative diagnostic methods with the optical image of an operating microscope in the correct position, orientation and scale. In order to achieve this, the position and the orientation of the operating microscope as well as the currently selected magnification and plane of focus must additionally be detected. In the known navigational systems this detection of position and orientation of the operating microscope takes in most cases place by providing reflecting markings on the microscope which, just like the aforementioned markings on the pointer, are detected by said two cameras on the aforementioned tie-bar. Moreover, there is a known system according to which the relative position and orientation of the microscope is detected by means of angle of rotation transmitters in the microscope carrier system. The disadvantage in said last-mentioned systems resides in that the carrier systems used therefore required a reinforcement so as to ensure a sufficient exactness, which renders them disproportionately heavy and expensive. The overlapping itself may then, for example, be effected by reflecting the CT- or MR-image into the optical observation beam path of the microscope by means of a projector.

The navigational systems according to the prior art show some substantial disadvantages. This includes, inter alia, the fact that the markings on the surgical instrument or, respectively, on the pointer must at any time be visible to the pair of stereo cameras disposed on the camera arm. If the markings are covered, the functional capability is negatively influenced and errors in the data acquisition occur. According to experience the so-called position-identifying times of optical, but also of magnetic navigation systems are about $\frac{2}{3}$. In addition, the large distance between the markings of the known optical instruments and the camera pair causes large measuring inaccuracies in the optical measurement, and relatively large-volume markings are required.

Another problem with current neurosurgical navigational systems resides in the motion of the brain tissue after the skullcap was opened and during the operation. This fact called brain shift results in that the geometry of the tissue during the operation no longer unlimitedly corresponds to the geometry of the tissue during the preoperative diagnostic method. This leads to errors, for example, in the aforementioned position indication of a pointer instrument relative to the tissue structures in a preoperative diagnostic MR- or CT-image. The error as described may be corrected, for example, by tracking the change of location of the tissue surface in the surroundings of the field of operation during the operation. To this end, the surgeon must, however, repeatedly tap on and mark several points on the aforementioned tissue surface with a marking instrument of the navigational system so as to make the data required for this correction available to the system. Given the stress, which in a neurosurgical operation is high enough anyhow, this constitutes a disadvantage, however.

By taking into account the aforementioned disadvantages of the prior art, the aim of navigational systems to be newly provided therefore resides in allowing a three-dimensional measurement of the field of operation and a tracking of the trajectories of the tip of the operating instrument, and in achieving an increased position identification, especially in the case of optical navigation. In addition, the large, expensive and occlusion-susceptible camera tie-bars are to be avoided. The handling of the systems is to be made simple and easy to survey so as to preclude error sources right from the beginning.

SUMMARY

According to the above it is, therefore, the object of the invention to provide an apparatus, system and method for optimizing the identification of the current position in navigation, especially neuronavigation, in surgery, which is based on an operating microscope known per se and at least one optoelectronic image receiver coupled to the observation beam path of the microscope.

Moreover, a partial object of the invention resides in creating a novel navigational instrument, especially for use in operations by means of an operational microscope.

The object of the invention is provided by an operating microscope and associated method for optimizing the identification of a current position. The operating microscope includes an optoelectronic image receiver, preferably a photonic mixer device (PMD), to detect a topography of a situs relative the microscope, and a modulated illumination device associated with the PMD to provide modulated illumination light.

In a preferred aspect, the PMD is arranged such that a sensor axis of the PMD is parallel to an optical axis of an observation beam path of the optoelectronic image receiver. Similarly, it is also preferred the observation beam path and the PMD are positioned at a common distance from the situs. Specifically, light from the situs travels a similar path, both in distance and angle, to the observation beam path and the PMD.

In additional aspects, optical filters are provided to protect the PMD from intensive illumination by unmodulated light, and the PMD detects markings on the situs, the markings including at least one of infrared reflectors or light emitting diodes. Further, a device is provided to generate a three-dimensional image of the situs from an image received from the optics of the microscope and the topography of the situs detected by the PMD.

In yet a further aspect, provided is an operating microscope including an optical unit for forming an image of an object plane in oculars of the microscope, an optoelectronic image receiver coupled to the microscope and optics to form images, of objects placed in a region between a front objective of the microscope and an object plane of the microscope, on the optoelectronic image receiver. The microscope has a magnification factor of the optics to form images, and a system to detect optical markings forming a markings pattern placed on a surgical instrument or an object placed in the region between the front objective of the microscope and the object plane of the microscope. The system calculates a geometrical position and orientation of the markings pattern in relation to the optoelectronic image receiver, relative the microscope.

Accordingly, the basic idea of the invention is to improve the position-identifying time of a navigational system by including the images from or parallel to the observation channels of the operating microscope in the actual image analysis of said system and to achieve additional advantageous effects, especially under the aspect of improving the exactness of the positional determination.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 1:
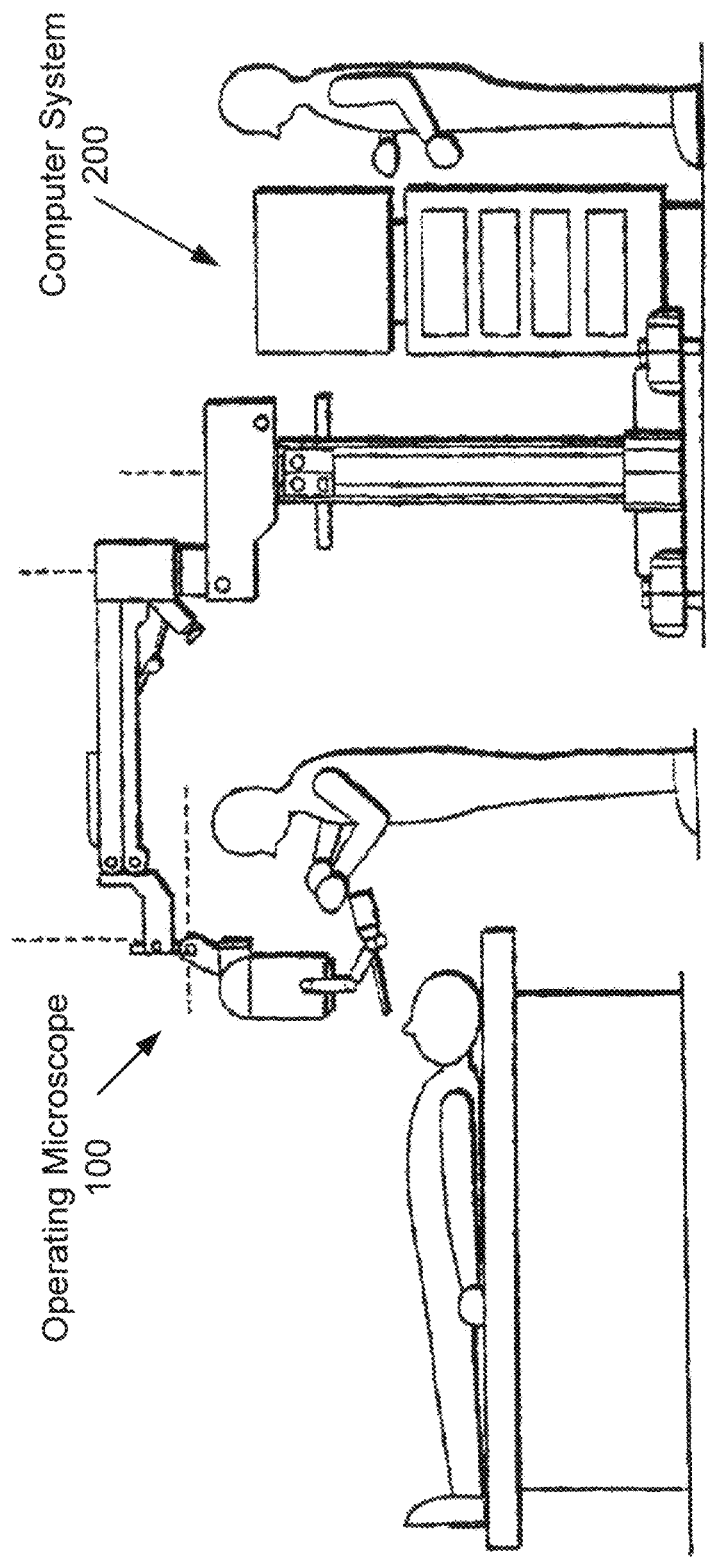
FIG. 1 is a schematic illustration of a surgical suite according to aspects of this disclosure, including a navigation system.

Data obtained from the at least one image receiver, each of which lie in the microscope field-of-view of the operator, contain information about the location of the operating instrument or pointer as used, especially of the tip thereof, wherein the actual position of the instrument in the x- and y-direction as well as in the z-direction of a three-dimensional coordinate system is continuously or intermittently determined from the relevant location data. For the positional determination in the z-direction either a distance determination is carried out by means of a depth of focus evaluation, or a stereoscopic image analysis is performed. Instead of two cameras with a stereoscopic image analysis also a novel optoelectronic image receiver designated as PMD array (PMD: Photonic Mixer Device) may be used. The measuring method of these sensors is related to the "time of flight" distance measuring method, but achieves, by novel principles with a smaller amount of apparatus and substantially smaller construction sizes, a better measuring exactness and may additionally be designed as a sensor array, with the result that it becomes feasible for the representation of an area to be topographed on a PMD array to obtain a complete topography with one measurement only. Since, due to the topography of a pointer, the pointer and the suitably formed markings thereof are easy to separate before the background of the field of operation, such a PMD array may also be used for tracking said pointer. If a PMD sensor is used, the object field of the sensor must be illuminated with an appropriately modulated and preferably narrow-banded light source, and the background light as well as the unmodulated white light of the operating microscope must be discriminated by suited filters prior to impinging the PMD array.

The optoelectronic image receiver(s) may directly be coupled to the observation beam path, especially by means of a beam splitter, wherein it also possible, however, to provide at least one separate image receiver beam path not being dependent on the observation beam path, which is likewise directed to the microscope field-of-view of the operator.

According to an embodiment the location of the operating microscope in space is detected, and said operating microscope positional data are supplied to a computer system known per se so as to transform the instrument positional data into a higher ranking space coordinate system by including existing data on the current position of the patient and preoperatively obtained three-dimensional data from the interior of the patient.

According to one embodiment of the invention it is possible, beside the data acquisition for the intraoperative location and position determination of a navigational instrument by means of known optical and/or magnetic methods, to carry out a supplementary three-dimensional position detection by means of the data provided by the image receiver of the operating microscope.

When using said two independent redundant systems, the hereinafter mentioned advantageous possibilities arise. If one of the systems does not supply any valid measured values, for example due to the covering of the markings, the measured values of the respective other system may be used, thereby allowing an increase of the position-identifying time. In case of redundant valid measured values the exactness of the measurement may be increased, for example, by averaging. In case of redundant valid measured values also the uncertainty of the measured values, e.g. due to the difference of the redundant measured values, may be quantified, whereby, for the first time, a navigational system is created which is more or less capable of performing a self-control. Even though the latter is standard for the major part of medical apparatus being critical for the safety of patients, it has so far not been realized in known navigational systems.

For detecting the location of the operating microscope in space a module is provided as an alternative to the known methods, which is integrated in the microscope or at least is connected with the microscope in a fixed and positionally invariant manner, which may do without the use of the space-filling tie-bars with cameras used in known systems and to be positioned next to the operating table. This module allows the microscope to detect its relative position in space or relative to the patient "by itself". Therefore, numerous components and measuring methods may be individually or in a combination thereof. For minimizing the size of the aforementioned module, required infrastructure (power supply mechanisms, computers etc.) may be integrated, for example, in the base of the carrier system.

If the microscope "itself" is able to determine its position in space or, respectively, relative to the patient, and if also the tracking of the pointer is realized without the stereo camera pair of the conventional navigational system, the stereo camera pair of the conventional navigational system may be dropped. In this case, space in the operating theatre is considerably saved. Moreover, the initiation is facilitated since fewer devices with fewer cables have to moved and operated before the operation starts and, furthermore, the danger of occlusions during the operation is eliminated or at least considerably reduced.

With respect to the problems involved by the so-called brain shifting it is provided according to the invention to arrange marking points at or on the tissue surface of the patient, the change of location of which detected by the image receivers and determined by the computer system is used to carry out a correction of preoperatively obtained data in relation to the current state.

As is known, a stereoscopic light microscope may either consist of two convergent monocular mono-objective microscopes, or may comprise two optical channels brought out of center behind a common front lens. Due to construction-specific advantages operating microscopes are nearly exclusively structured as so-called common main objective (CMO) microscopes. The modeling of a CMO-microscope in an optical view is, however, extremely difficult as the treatment of so-called skew light beams becomes necessary. This is based on the lateral displacement of both optical channels behind the aforementioned common front lens.

If a stereoscopic analysis for neuronavigation becomes necessary, the person skilled in the art will at first preclude the use of CMO-microscopes by taking into account the aforementioned problems.

This prejudice is overcome herein by finding an exclusively analytic formulation of the microscope model, which eventually corresponds to two rectified pin diaphragm cameras where corresponding points in both views theoretically lie on the corresponding image parts. By this finding the additional image processing steps may strongly be facilitated and image processing techniques known per se may be used.

Therefore, in accordance herewith, the data obtained by the image receiver provided for each channel are corrected in view of the distortion errors in the x- and y-direction and in view of the disparity errors in the z-direction. This correction depends of the respective adjustments of the microscope, i.e. zoom and focus.

For the error correction a calibration is at first performed wherein, as was mentioned above, the operating microscope is described as a two-pin diaphragm camera on the image side. The calibration is carried out for all zoom and focus stages. The obtained calibration data are stored so as to allow an online or offline error correction at a later time. Of course, it is possible to store microscope-specific error correction data in a look-up table, so that the actual correction process can be facilitated under a calculation-technical aspect and thereby shortened.

All physical quantities required-for calculating the nominal pin diaphragm camera parameters for a CMO-microscope are easily accessible and can typically be inferred from the manufacturer's data sheet. Initial values for an iterative calibration may be measured on the microscope in an easy manner. The required data concerning the image receivers, e.g. CCD sensors, are likewise available as manufacturer's data. The knowledge of internal lens data is not necessary. The CMO-microscope-adapted stereoscopic image processing is accomplished by a method in which the representation from both two-dimensional camera planes is formulated into the three-dimensional space by polynominal approximations of a smallest possible degree. A required control point quantity acts as supporting point quantity for the polynomials and is chosen in the entire volume.

For the practical application of microscopes with a continuously variable zoom and/or focus, it is proposed to calibrate the individual system parameters in several zoom and focus settings and, when setting intermediate values, to interpolate the corresponding system parameters from the calibrated supporting points. The current settings of zoom and focus are to be made available to the analyzing unit during the calibration procedure, but also during the measuring procedure, advantageously by the microscope via a data line.

In connection with the novel navigational instrument, especially for use in a method using image information from the beam path of a neuronavigational operating microscope, markings, especially micromarkings, are provided in the proximity of the instrument tip, namely basically when used lying in the field of view of the microscope. A certain minimum interspace to the instrument tip is due to the necessity that the markings are not to be contaminated by blood or other body liquids and, in case of convex markings, the use of the pointer instrument must not be obstructed.

The markings may, for example, be formed as at least three coplanar colored balls lying in one plane, which extends parallel to the longitudinal axis of the instrument, but does not include the same. Other embodiments are constituted by colored or reflecting annular markings. If the microscope is to be operated over a particularly large zoom and focus range, it may happen that the markings no longer completely lie in the field of view of the microscope if the magnifications are particularly strong and the lengths of focus too short, or that the markings are too small if the magnifications are particularly weak and the lengths of focus are large. In this case it is useful to attach several sets of markings having different sizes, wherein the smallest set of markings points or is attached closest to the instrument tip.

The navigational instrument according to the invention is sterilizable and can well be recognized through the microscope. Its one end is formed as a marked tip and may be employed as pointer. In the case where the tip is not directly visible for operative reasons, it can be detected via the aforementioned markings and the other information relating to the shape of the instrument.

The increased position identification in the case of optical systems is achieved by that the image recording is directly effected by the microscope, whereby it is ensured that the navigational instrument is not covered by the fingers or another operating set. The risk of covering by operating staff, as takes place with conventional optical navigational systems, is here precluded from the very beginning. Due to the ability to measure relative distances of points in the coordinate system of the microscope a further possibility consists in differential navigation, i.e. distances from points to a reference point can be measured.

In contrast to navigational instruments on the market so far the markings according to the invention are positioned close to the tip. Since a navigation is effected through the microscope, moreover, far smaller markings may be used. This, again, makes it possible to fabricate the navigational instrument itself smaller and more inexpensively and, above all, to use the same more flexibly and more ergonomically.

An exemplary navigational instrument is formed as a bayonet-type round steel of substantially 4 mm, tapered over a range of substantially 30 mm at the tip. The bayonet-like shape or cranking is useful under the aspect that it can be excluded that the instrument is covered by fingers or the like for the area detected by the camera.

According to one embodiment, the aforementioned coplanar balls are used as markers, which have, for example, a diameter of about 1.5 mm. For rendering the segmentation of the balls against the background as simple as possible, the same are lacquered in different colors. In view of the specific properties of the situs, blue, green and violet and/or brilliant yellow are preferably used. The use of infrared-reflecting balls is likewise possible, as is light emitting diodes (LED).

Since the work may be performed with the light source provided on the microscope's side, the embodiment with colored markings can do without special ball coatings which reflect infrared radiation, for example, according to a distinct directional characteristic.

A further development resides in that the marker configuration is not placed upon and attached to the navigational instrument, but merely consists of overprints. In case of the required detection of the rotation of the navigational instrument about its own axis an angle coding extending in an azimuthal direction is, for example, conceivable.

The detection of the balls in the camera views is preferably accomplished by applying colored image processing methods. In dependence on the intensiveness of a possibly existing color cast, the same is directly compensated with the image recording by a white balance. To this end, a scaling of the intensities of the red and blue channel of each image receiver or each camera, respectively, takes place.

The feature extraction or pattern recognition, respectively, of the markings in the form of coplanar colored balls is effected by the fact that a ball-shaped object is imaged in a differentiated manner. If the central point of the ball does not lie on the vertical of the camera plane, the contour of the ball is projected as an ellipse. The form therefore allows conclusions to the position of the individual balls.

If the instrument tip is not directly visible in the camera images, the three-dimensional position of the pointer tip is determined from the three-dimensional positions of the ball centers.

Of course, the navigational instrument may also be formed of a common operation set in order to not unnecessarily interrupt the operation for navigational purposes.

For calculating the three-dimensional coordinates of the tip position from the three-dimensional ball centers, the underlying geometry is calibrated. To this end, a local instrument coordinate system originating from a ball in the middle is defined, from which two axes extend through the other two balls and the third axis is orthogonal to the so spanned plane. In this affine coordinate system the location of the pointer tip has three definite coordinates, so that it may be reconstructed indirectly via the reconstruction of the axes of the local instrument coordinate system. The affine coordinates are independent of the intrinsic or extrinsic parameters of the camera arrangement and can be calibrated for a number of predefined tip and ball coordinates.

Herein, the terms position and location are substantially used as synonyms. It lies within the range of knowledge of the person skilled in the art that, for detecting the location of a three-dimensional body in space, six coordinates, e.g. emission point/center of gravity or the like are to be indicated in x-, y- and z-orientation and with the three so-called Eulerian angles. One exception is only constituted by the instrument tip, which only requires three coordinates as spatial point for defining the location.

The disclosure will hereinafter be explained in more detail by means of embodiments.

First Embodiment

According to a first embodiment the field of operation lies inside the head of a patient, and an operating instrument is positioned with a corresponding marking in the field of view of the operating microscope.

The images of both observation channels are led via a beam splitter to two image receivers, e.g. CCD cameras. The camera images are then evaluated by a computer, and the position of the operating instrument is calculated in the coordinate system of the microscope from the stereoscopic image analysis and the device parameters, such as zoom and focus settings, which are additionally outputted by the microscope via a data connection.

At the same time, the location of the microscope and the patient is detected in the coordinate system of the stereo camera arm by a stereo camera pair with corresponding cameras, which is positioned in the proximity of the operating table, by means of stereoscopic image analysis and with the aid of the patient markings and the microscope markings. This allows the offsetting of the coordinate systems of the microscope and the patient and, for example, the position of the operating instrument may be indicated in coordinates of the patient.

Optionally, markings on the operating instrument may additionally be detected and evaluated by the camera pair, which results in a redundant measurement of the determination of the position of the operating instrument.

According to another embodiment, a generation of marking points, lines or a grating into the field of view of the microscope may be performed with visible light or with radiation in the near-infrared range. Said marking points, lines or gratings can then be recorded with a corresponding camera coupled to one of the observation channels. By evaluating the camera image, the location of the marking points can be detected in coordinates relative to the microscope.

Technically, the aforementioned teaching can be realized by that light is led via a diaphragm into the observation channel of the operating microscope and is imaged on one spot in the plane of focus of the microscope. This light spot is then detected by a camera, especially a CCD camera. With known coordinates in x- and y-direction of the diaphragm aperture in a Cartesian coordinate system perpendicular to the optical axis it then becomes possible, together with coordinates of the light spot on the camera chip, to work analogously to the common stereoscopic image analysis. Thus, the location of the spot, on which the light entering though the diaphragm is imaged, can be determined in coordinates of the microscope. As was mentioned above, light projection systems may be used instead of the illuminated diaphragm, each of which project a number of points, lines or gratings into the field of operation.

In case of a light grating, crossing points may be detected by the cameras. By means of the stereoscopic image analysis the coordinates of the crossing points of the light grating are then determinable on the surface of the field of operation in the coordinate system of the microscope. The information derived therefrom can then be represented as a three-dimensional perspective grating in the form of contour lines or the like on a display and may be used for the allocation of the location relative to preoperative recordings.

As part of quality assurance video recordings and photographs are, in most cases, made in today's operating theatres. Said video recordings and photographs do neither contain any quantitative three-dimensional information, nor can those generally be extracted from said video recordings and photographs.

If the recording of topographies of the field of operation during the operation is successful with an acceptable amount of work involved, the lack of the quantitative 3D-information of today's documentation would be inapplicable. Such topographies can be stored without problems and, within the framework of quality-assuring measures, for example, the actual resection profile can be compared with the findings from preoperative diagnostic data, such as the magnetic resonance tomography and the computerized tomography. Corresponding topographies may also be visualized to the doctor, for example, as relief diagrams, already during the operation. Thus, it becomes possible—in addition to post-operative quality assurance—to offer decision aids for optimizing the resection boundaries to the surgeon already during the operation.

In principle, a topography of the object field of the microscope can already be obtained with the above-described microscope comprising stereo cameras by means of common stereoscopic image analysis methods. Especially the correspondence analysis is, however, very time-consuming and susceptible to errors for natural, possibly weakly structured fields.

An improvement can be achieved by the following description of the methods and devices, inter alia, for the projection of light markings.

By means of light markings the corresponding points required for the stereoscopic image analysis can be determined fast, precisely and with an extremely low error rate.

One possible first embodiment makes use of stereo cameras permanently connected to the microscope and a projection system which need not necessarily be permanently connected to the microscope.

A second embodiment is based on the light projection device at the location of one of both stereo cameras, with the use of the optical channels/paths which were used in the first mentioned embodiment by exactly this camera. In this case the methods of stereoscopic image analysis can already be applied with one camera only, which is known by the term inverse camera.

According to another embodiment the topography is obtained directly from the data of a PMD array (PMD: Photonic Mixer Device) and an associated personal computer.

According to the first embodiment a generation of marking points, lines or gratings into the field of view of the microscope may be performed with visible light or with radiation in the near-infrared range.

The tissue in the field of view of the operating microscope can then be recorded together with the marking points, lines or gratings projected onto said tissue by two cameras which are, for example, coupled to the observation channels of the microscope. By evaluating the camera images with the stereoscopic image analysis the location of the marking points can be detected in coordinates relative to the microscope. The principal error source of the stereoscopic image analysis—the correspondence analysis—is thereby drastically facilitated and error-proof, since only the marked points of both camera images are included in the evaluation, in connection with which the uncertainty of the correspondence allocation is essentially smaller than with unmarked points.

For obtaining a topography of the marked points in coordinates of the patent—instead of in coordinates of the microscope—the relative location and orientation of the patient and the microscope must be detected, which may be accomplished in the explained manner.

Second Embodiment

The procedure according to the second embodiment is largely analogous to the first embodiment. Instead of the two cameras coupled to the observation channel of the microscope, however, one of the cameras is replaced by a diaphragm. The same lens system, which had previously imaged the object field onto said camera, is now used to image the diaphragm onto the object field. If a diaphragm structured with points, lines or gratings is used, and light is led through said diaphragm structures and the associated optical channel onto the object field, and if the correspondingly illuminated area is recorded with the remaining camera, the principle of the inverse camera is applicable, and the methods of stereoscopic image analysis are usable despite the use of one camera only. With respect to the error security here, too, the advantages of the first embodiments apply. If invisible light is used, visible light may additionally be admixed so as to make the supporting points of the topography visible already in the image of the ocular of the microscope.

Third Embodiment

In a third embodiment a PMD sensor array is used instead of the conventional cameras. For being able to use the same, modulated light must be used for illumination in addition to the visible light of the microscope. The PMD sensor is protected against a too intensive illumination by the white non-modulated light by suited optical filters. The topography of the field imaged on the PMD sensor array may be obtained with this new technology directly from the PMD chip with an associated computer having a suited interface.

The topographical data obtained in the above embodiments can then, for example, as three-dimensional perspective grating or in the form of contour lines or the like, be represented on a display. Moreover, said topographical data can be represented location-correlated with data from preoperative diagnostic data (nuclear resonance scanning data, computerized tomography data etc.).

Fourth Embodiment

In a fourth embodiment, which is an enhancement to the third embodiment, the PMD sensor array is provided as a component of the surgical microscope.

FIG. 1 illustrates a surgical suite, including a patient, a surgeon, an assistant, an operating microscope 100 and a computer system 200. A portion of the operating microscope 100 is shown schematically in FIG. 2. The operating microscope 100 in this embodiment includes an observation beam path portion 102, preferably for stereoscopic inspection, and a tracking camera 104 positioned proximate the observation beam path portion 102, the tracking camera 104 detecting a topography of a situs.

In preferred aspects, the tracking camera 104 is a PMD sensor array and is arranged such that a sensor axis of the PMD sensor array is parallel or substantially parallel/coaxial to an optical axis of the observation beam path portion 102, where the optical axis is of the common main objective of the operating microscope 100. In additional preferred aspects, a front objective of the observation beam path portion 102 and the tracking camera 104 are arranged at a common distance from the situs to have a common angle of receiving an image and detecting a topography, respectively, of the situs. The tracking camera 104 detects a topography and space positions of markings in a visual field thereof and, since it is a part of the operating microscope 100, the detection is relative to the position of the observation beam path portion 102.

Figure 2:
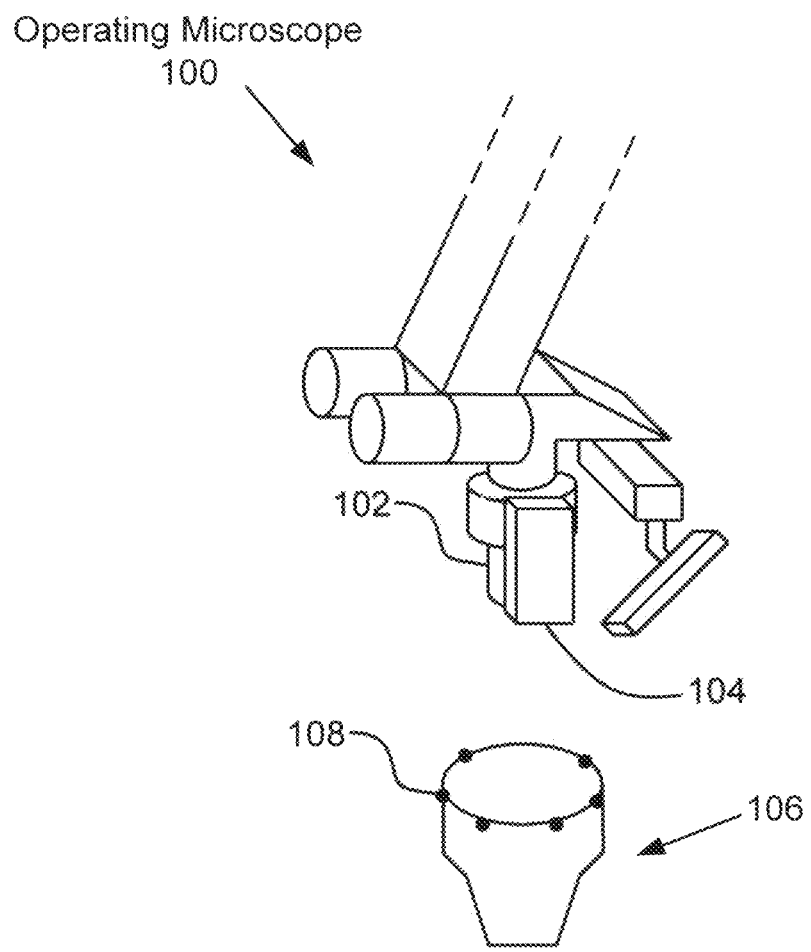
FIG. 2 is a schematic diagram of a navigation system including a tracking camera positioned above a schematic drawn skull.

As shown in FIG. 2, the operating microscope 100 is positioned above a schematic diagram of a skull 106. The skull 106 includes markings 108. As discussed above, the markings 108 can include infrared reflectors, similar to an arrangement of reflective balls, or LEDs. Markings can also be provided on surgical instruments (not shown) which identify the surgical instruments. Specifically, markings patterns can be predefined and electronically stored in a storage unit to identify detected surgical instruments. Further, the surgical instruments can be correlated, in the storage unit, with predefined geometrical shapes for tracking and displaying with preoperative measurements of the situs or a currently obtained topography of the situs.

The field of view of the tracking camera 104 partly overlaps the object plane of the operating microscope 100. The markings 108 are generally outside the field of view of the operating microscope 100. Nonetheless, the markings 108 still need to be detected. By using the tracking camera, though, it is not necessary to use a stereo camera pair, as previously discussed.

Figure 3:
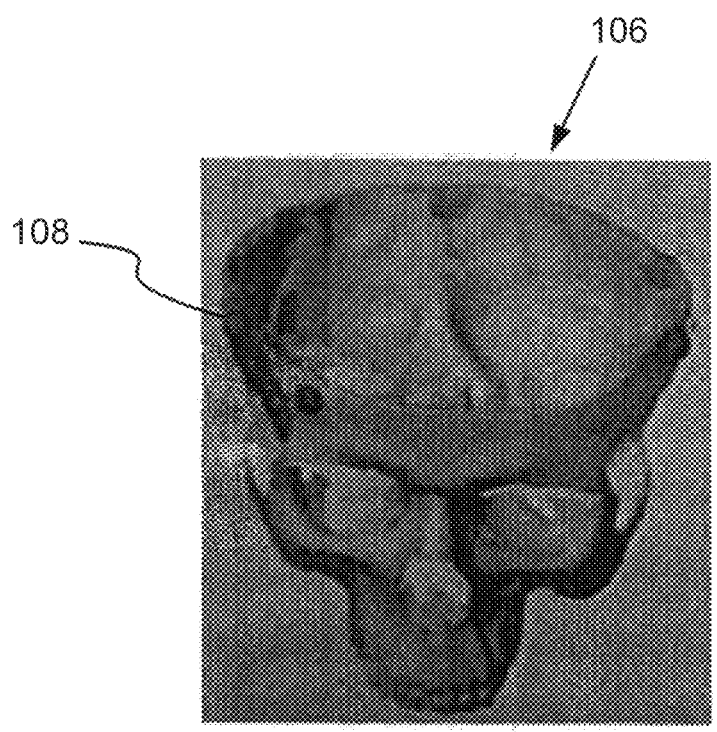
FIG. 3 is a generated three-dimensional image of the skull schematically shown in FIG. 2.

As a result, by combining an image from the observation beam path portion 102, which is preferably a stereoscopic image, with a topography image from the tracking camera 104, a three-dimensional image can be generated. For example, a three-dimensional image (by use of the computer system 200) can be generated from the skull 106 and the markings 108 by the operating microscope 100, as is shown by example in the image shown in FIG. 3. As noted above, but not shown, the image may include a surgical instrument.

As a result, this fourth embodiment is operational with only one tracking camera (i.e., only one single measurement camera other than the functional components and optics of the operating microscope 100), and the following advantages are obtained:

Since the tracking camera receives the same alignment as the observation beam path/common main objective of the operating microscope, any problems caused by an obstructed view are largely removed. This leads to an improvement of the presence time and ergonomics of the navigation system, and thus, to a shorter operation time and minimization of complications.

The measurement volume of the tracking camera is reduced considerably (comparatively), which leads at the same time to a greater accuracy of the measuring system. Also, the navigation aids can be miniaturized correspondingly, so that the workspace in the operation room is not limited.

The required processing on the computer system 200 and/or a visual display (i.e. video processing) can be integrated into an existing video documentation system of the microscope. Therefore, double work steps (entering patient information, documentation, etc.) during/pre operation can be avoided. Space can also be reduced.

The combination of two cost-intensive apparatuses results in a considerable cost optimization.

Figure 4:
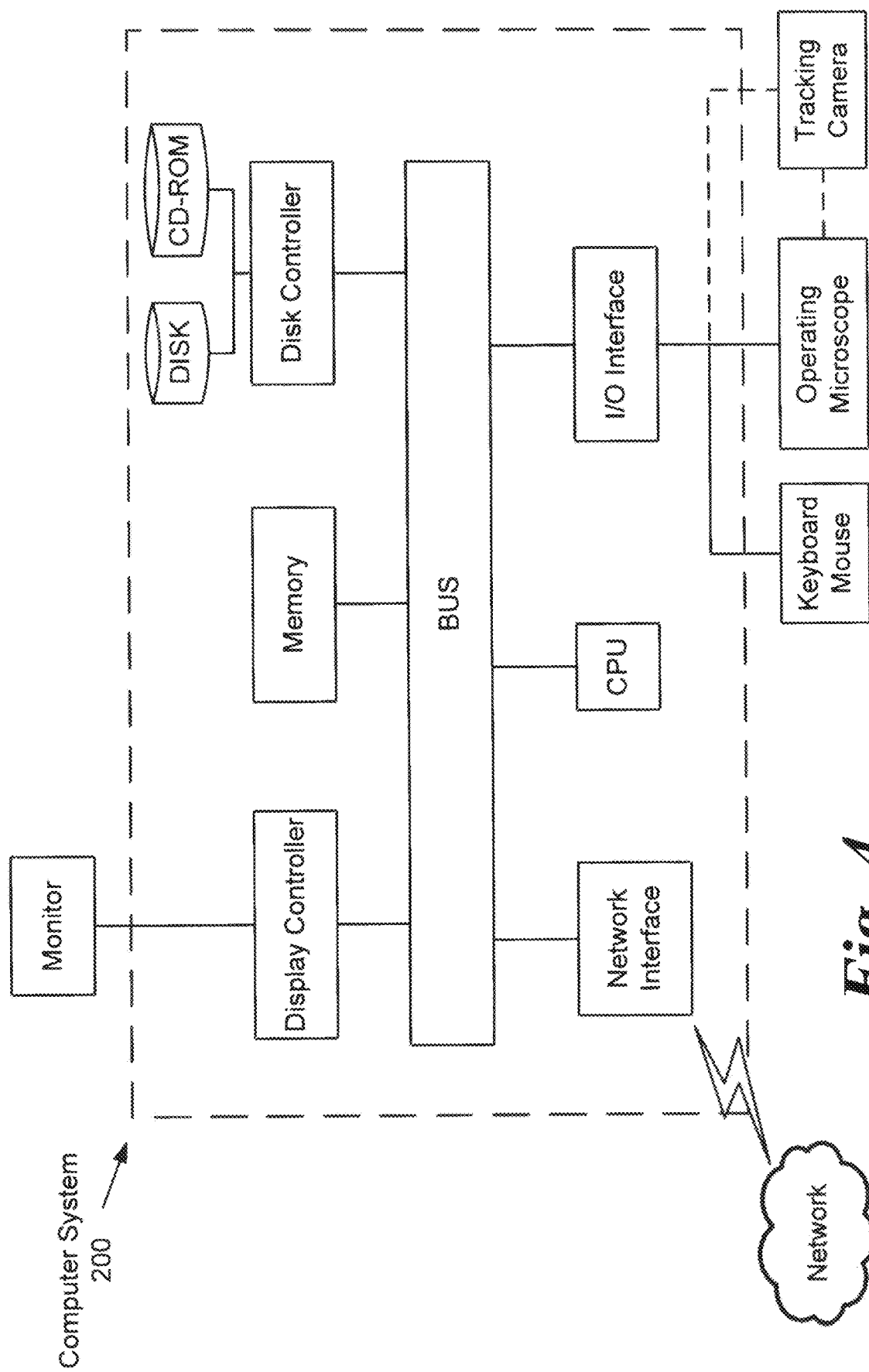
FIG. 4 is a schematic diagram of a computer system for processing the various algorithms and processes described in this disclosure.

An example of the aforementioned computer system 200 is shown in FIG. 4, and includes various computer components, including a central processing unit, memory devices, a controller connected to a display, a network interface connected to a network, and an input/output interface connected to or connecting input peripherals and the aforementioned operating microscope and tracking camera.

As discussed above, with the use of a PMD sensor array as the tracking camera 104, it is possible to highly integrate the PMD sensor array with the operating microscope 100, including the processing aspects of the computer system 200. Accordingly, it is not necessary that the computer system 200, as shown in FIG. 1, be a separate machine, but that it is possible for the functional components of the computer system 200 to be incorporated into the operating microscope 100 or as part of an existing video processing/recording component of the operating microscope 100.

Figure 5:
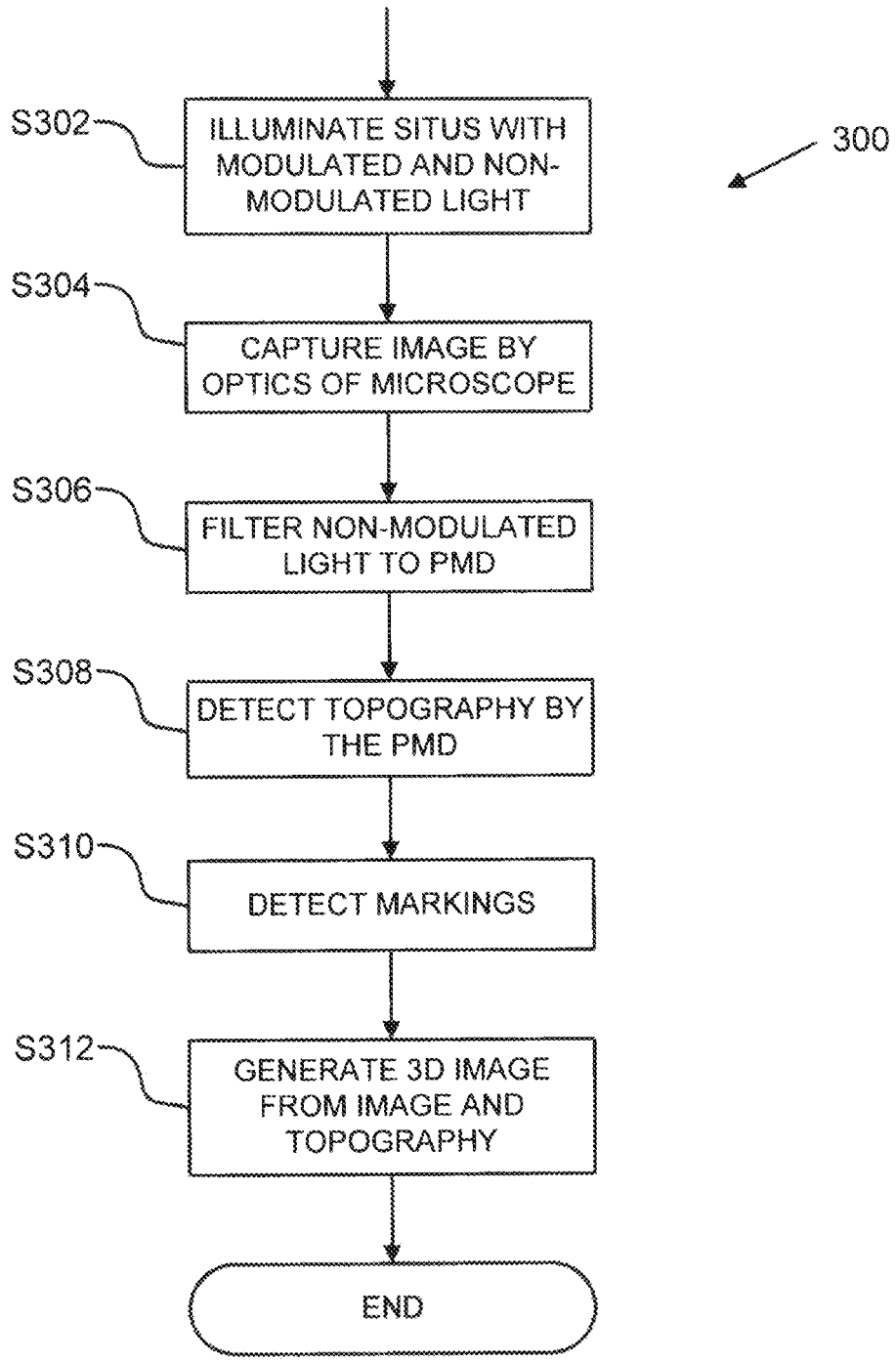
FIG. 5 is a flowchart depicting a process and algorithm in accordance with preferred aspects of this disclosure.

In a preferred aspect, operation of the fourth embodiment is consistent with the algorithm 300 shown in FIG. 5. As such, the situs is illuminated with unmodulated light and modulated light at S302. An image of the situs is captured at S304 by the optics of the microscope (from the non-modulated light), and at S306, non-modulated light directed to the PMD is filtered from the PMD to protect the PMD from intensive illumination by the non-modulated light. At S308, the topography of the situs is detected by the PMD of the microscope (from the modulated light illuminating the situs). Further, the markings on the situs are detected by PMD at S310, and finally, a three-dimensional image of the situs is generated from the image captured from the optoelectronic image receiver and the topography of the situs detected by the PMD.

As noted above, the generating can be performed by computer equipment similar to the computer system shown in FIG. 4. However, as presented above, since the computational requirements in the fourth embodiment are reduced, the functional components of the computer equipment can be a component of the operating microscope.

What is claimed is:

1. An operating microscope having an observation beam path and an object plane, said microscope comprising:
   a main objective and optics forming an image of the object plane;
   an optoelectronic image receiver arranged to continuously or periodically detect a topography of a surgical situs in front of the main objective, and generate topographical data representative of said topography;
   a computer connected to receive said topographical data, said computer including memory and a processor;
   preoperative diagnostic data of the surgical situs stored in said memory for use with said topographical data;
   wherein the computer location-correlates said topographical data with said preoperative diagnostic data to produce location-correlated topographical data, and presents said location-correlated topographical data in the form of a perspective grating or contour line on an image generated from said preoperative diagnostic data on a display, said perspective grating or contour line changing to reflect changes in said topographical data resulting from removal of tissue or a change of position of tissue during an operation.

2. The microscope according to claim 1, wherein:
   said optoelectronic image receiver comprises a photonic mixer device (PMD), to detect the topography of the situs relative to the microscope; and
   a source of modulated illumination associated with the PMD.

3. The microscope according to claim 2, wherein the PMD is arranged such that a sensor axis of the PMD is coaxial to the observation beam path.

4. The microscope according to claim 2, further comprising:
   optical filters positioned to protect the PMD from intensive illumination by unmodulated light.

5. The microscope according to claim 2, wherein the PMD detects optical markings forming a markings pattern on a surgical instrument or an object placed in front of the main objective of the microscope.

6. The microscope according to claim 1, wherein light from the situs passes through the main objective of the microscope before reaching the optoelectronic image receiver.

7. The microscope according to claim 1, wherein the optoelectronic image receiver includes a stereo camera pair with a computing system to perform stereoscopic analysis.

8. The microscope according to claim 7, further comprising:
   a device configured to project a light pattern onto the situs, the light pattern captured by the stereo camera pair for improved correspondence analysis of the stereoscopic images.

9. The microscope according to claim 1, wherein the optoelectronic image receiver is a single camera with a computing system to perform stereoscopic analysis by operating the single camera as an inverse camera, the operating microscope further comprising:
   a device configured to project a light pattern onto the situs.

10. The microscope according to claim 1, wherein the topography is transmitted to a navigational system, and the navigational system correlates the topography as a starting point for correction of a brain shift.

11. The microscope according to claim 1, wherein a focus of the operating microscope is adjusted based on the topography.

12. The microscope according to claim 1, wherein the optoelectronic image receiver detects a position of a surgical instrument, or a pointer directed toward the situs, said position is extracted from the topography relative the at least one optoelectronic image receiver, respective to the microscope, and
   the position of the surgical instrument, or the pointer, is transmitted to the navigational system for referencing or displaying the position of the surgical instrument, or the pointer, in the topography within the location-correlated preoperative diagnostic datasets of the situs.

13. The microscope according to claim 1, wherein the topography is detected continuously or periodically during an operation.

14. The microscope of claim 1, wherein said computer includes an algorithm to process said topographical data to generate said location-correlated topographical data.

15. A method of providing information to an operator of a surgical microscope having an observation beam path and an object plane comprising:
   providing a main objective and optics forming an image of the object plane;
   arranging an optoelectronic image receiver to continuously or periodically detect a topography of a surgical situs in front of the main objective, and generate topographical data representative of said topography;
   connecting a computer to receive said topographical data, said computer including memory and a processor;
   storing preoperative diagnostic data of the surgical situs in said memory;
   location-correlating said topographical data with said preoperative diagnostic data to produce location-correlated topographical data;
   presenting said location-correlated topographical data in the form of a perspective grating or contour line on an image generated from said preoperative diagnostic data on a display;
   wherein said perspective grating or contour lines change to reflect changes in said topographical data resulting from removal of tissue or a change of position of tissue during an operation.

16. The method of claim 15, wherein said step of arranging an optoelectronic image receiver includes said optoelectronic image receiver comprising a photonic mixer device (PMD) to detect the topography of the situs relative to the microscope and a source of modulated illumination associated with the PMD.

17. The method of claim 16, wherein said step of arranging an optoelectronic image receiver includes positioning the PMD such that a sensor axis of the PMD is coaxial to the observation beam path.

18. The method of claim 15, wherein said step of arranging an optoelectronic image receiver includes positioning a front objective of the microscope and the PMD at a common distance from the situs.

19. The method of claim 15, wherein said step of location-correlating said topographical data with said preoperative diagnostic data includes the computer processing said topographical data with an algorithm to generate said location-correlated topographical data.

* * * * *